(12) United States Patent  (10) Patent No.: US 11,638,604 B2
Kobayashi et al.  (45) Date of Patent: May 2, 2023

(54) TREATMENT INSTRUMENT (71) Applicant: OLYMPUS CORPORATION, Hachioji (JP)

(72) Inventors: Marina Kobayashi, Hachioji (JP); Yuji Hirai, Sagamihara (JP); Eiji Murakami, Hachioji (JP); Tadashi Kitayama, Sagamihara (JP); Satoshi Miyajiri, Tachikawa (JP); Katsushi Ide, Hachioji (JP); Takahito Oshiro, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 481 days.

(21) Appl. No.: 16/515,632

(22) Filed: Jul. 18, 2019

(65) Prior Publication Data
US 2019/0336202 A1  Nov. 7, 2019

Related U.S. Application Data (63) Continuation of application No. PCT/JP2017/001526, filed on Jan. 18, 2017.

(51) Int. Cl.
A61B 18/14 (2006.01)
A61B 17/32 (2006.01)
A61B 18/00 (2006.01)

(52) U.S. Cl.
CPC .. *A61B 18/1445* (2013.01); *A61B 17/320016* (2013.01); *A61B 2018/00071* (2013.01);
(Continued)

(58) Field of Classification Search
CPC ........ A61B 18/1445; A61B 17/320016; A61B 2018/0071; A61B 2018/00589;
(Continued)

(56) References Cited

U.S. PATENT DOCUMENTS

2007/0043297 A1* 2/2007 Miyazawa ..... A61B 17/320092
600/471
2007/0198005 A1 8/2007 Ichihashi et al.
(Continued)

FOREIGN PATENT DOCUMENTS

CN 102596079 A 7/2012
JP 2007-050181 A 3/2007
(Continued)

OTHER PUBLICATIONS

Mar. 21, 2017 Search Report issued in International Application No. PCT/JP2017/001526.
(Continued)

*Primary Examiner* — Daniel W Fowler
*Assistant Examiner* — Annie L Shoulders
(74) *Attorney, Agent, or Firm* — Oliff PLC (57) ABSTRACT A treatment instrument includes a grasping piece that is openable and closable to a treatment portion, and includes an electrode member. An electrode inclination surface facing a side on which the treating portion is located is provided on an outer surface of the electrode member of the grasping piece, and the electrode inclination surface extends from an inner side to an outer side in a width direction so as to be inclined in a direction away from the treatment portion.

16 Claims, 4 Drawing Sheets (52) U.S. Cl.
CPC ............... *A61B 2018/00589* (2013.01); *A61B 2018/00601* (2013.01); *A61B 2018/00607* (2013.01); *A61B 2018/00845* (2013.01)

(58) Field of Classification Search
CPC ........... A61B 2018/00607; A61B 2018/00601; A61B 2018/00845
See application file for complete search history.

(56) References Cited

U.S. PATENT DOCUMENTS

| | | | | |
|---|---|---|---|---|
| 2008/0132887 | A1* | 6/2008 | Masuda | A61B 17/320092 606/37 |
| 2012/0101493 | A1* | 4/2012 | Masuda | A61B 17/320092 606/34 |
| 2012/0203143 | A1* | 8/2012 | Sanai | A61B 17/320092 601/3 |
| 2016/0051316 | A1* | 2/2016 | Boudreaux | A61B 18/1445 606/45 |
| 2017/0000516 | A1 | 1/2017 | Stulen et al. | |
| 2017/0000558 | A1 | 1/2017 | Inoue | |

FOREIGN PATENT DOCUMENTS

| | | |
|---|---|---|
| JP | 2008-011987 A | 1/2008 |
| JP | 2015-204974 A | 11/2015 |
| WO | 2007/097330 A1 | 8/2007 |
| WO | 2015/137139 A1 | 2/2015 |

OTHER PUBLICATIONS

Jul. 23, 2019 International Preliminary Report on Patentability issued in International Application No. PCT/JP2017/001526.
Sep. 17, 2021 Office Action issued in Chinese Patent Application No. 201780084040.0.
Mar. 15, 2022 Office Action issued in Chinese Patent Application No. 201780084040.0.
Aug. 31, 2022 Office Action issued in Chinese Patent Application No. 201780084040.0.

* cited by examiner

TREATMENT INSTRUMENT

CROSS-REFERENCE TO RELATED APPLICATIONS

This is a Continuation Application of PCT Application No. PCT/JP2017/001526, filed Jan. 18, 2017, the entire contents of which are incorporated herein by reference.

The present disclosure relates to a treatment instrument which grasps a treatment target between a treating portion and a grasping piece, and treats the grasped treatment target with treatment energy.

BACKGROUND

In a treatment instrument that can grasp a treatment target between a treating portion and a grasping piece, the treating portion has electrical conductivity and ultrasonic vibrations are transmitted to the treating portion. In addition, the grasping piece includes an electrode member having electrical conductivity, and a pad member having electrical insulation. In this treatment instrument, the ultrasonic vibrations transmitted to the treating portion are applied to the treatment target grasped between the treating portion and the grasping piece, as treatment energy. In addition, in a state where the treatment target is grasped between the treating portion and the grasping piece, electrical energy (high frequency electric power) is supplied to the electrode member of the grasping piece and the treating portion, and thus, a high frequency current flows to a portion between the electrode member and the treating portion through the treatment target. Accordingly, the high frequency current is applied to the treatment target as the treatment energy, and the treatment target coagulates.

BRIEF SUMMARY

According to one aspect, the present disclosure relates to a treatment instrument including: a rod which extends from a proximal side to a distal side in a longitudinal and includes, on the distal side, a treatment portion that has electrical conductivity; and a grasping piece which is openable and closable relative to the treating portion, and includes an electrode member that has electrical conductivity. The treatment portion includes a rod outer surface that faces the grasping piece The rod outer surface includes a first rod inclination surface that extends inward in the width direction from one side of the treatment portion so as to be inclined in a direction toward the grasping piece, and a second rod inclination surface that extends inward in the width direction from an opposite side of the treatment portion so as to be inclined in a direction toward the grasping piece. The rod outer surface also includes a rod parallel surface that is provided between the first rod inclination surface and the second rod inclination surface, and extends substantially parallel to the width direction. The electrode member includes an electrode inclination surface that faces a side on which the treating portion is located, and extends from an inner side to an outer side in the width direction so as to be inclined in a direction away from the treatment portion. The electrode member also includes an electrode facing surface that is disposed inside the electrode inclination surface in the width direction, and extends from an inner side to an outer side in the width direction so as to be inclined in a direction toward the treatment portion The grasping piece includes a pad member which is provided a first electrode facing surface and a second electrode facing surface in the width direction, and which has electrical insulation. The pad member includes a pad abutment surface which abuts against the rod parallel surface, and which is provided substantially parallel to the rod parallel surface.

According to another aspect, the present disclosure relates to a treatment instrument including: a rod that extends from a proximal side to a distal side in a longitudinal direction, and includes, on the distal side a treatment portion that has electrical conductivity; a grasping piece that is openable and closable relative to the treatment portion, and includes an electrode member that has electrical conductivity; and an energy source device configured to supply high frequency electric power to the electrode member and the treating portion. The grasping piece may be configured to move in a direction along a virtual plane that extends in a direction substantially parallel to an extending direction of the treatment portion and substantially parallel to opening and closing directions of the grasping piece. The treatment portion includes a rod outer surface that faces the grasping piece. The electrode member includes a first electrode portion and a second electrode portion. The second electrode portion is provided outside the first electrode portion in a width direction that intersects the virtual plane. The treatment instrument is designed to flow a high frequency current to a portion between the rod facing surface and the first electrode portion, and compress a living tissue at a first pressure between the rod outer surface of the treatment portion and the first electrode portion in a state where the living tissue is grasped between the grasping piece and the treatment portion. The treatment instrument is also designed to flow a high frequency current to a portion between the rod outer surface of the treatment portion and the second electrode portion, and compress the living tissue by the second electrode portion at a second pressure smaller than the first pressure in the state where the living tissue is grasped between the grasping piece and the treatment portion.

Advantages of the treatment instrument will be set forth in the description which follows, and in part will be apparent from the description, or may be learned by practice. The advantages may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate exemplary embodiments, and together with the general description given above and the detailed description of the embodiments given below, serve to explain the principles of the present disclosure.

DETAILED DESCRIPTION

Figure 1:
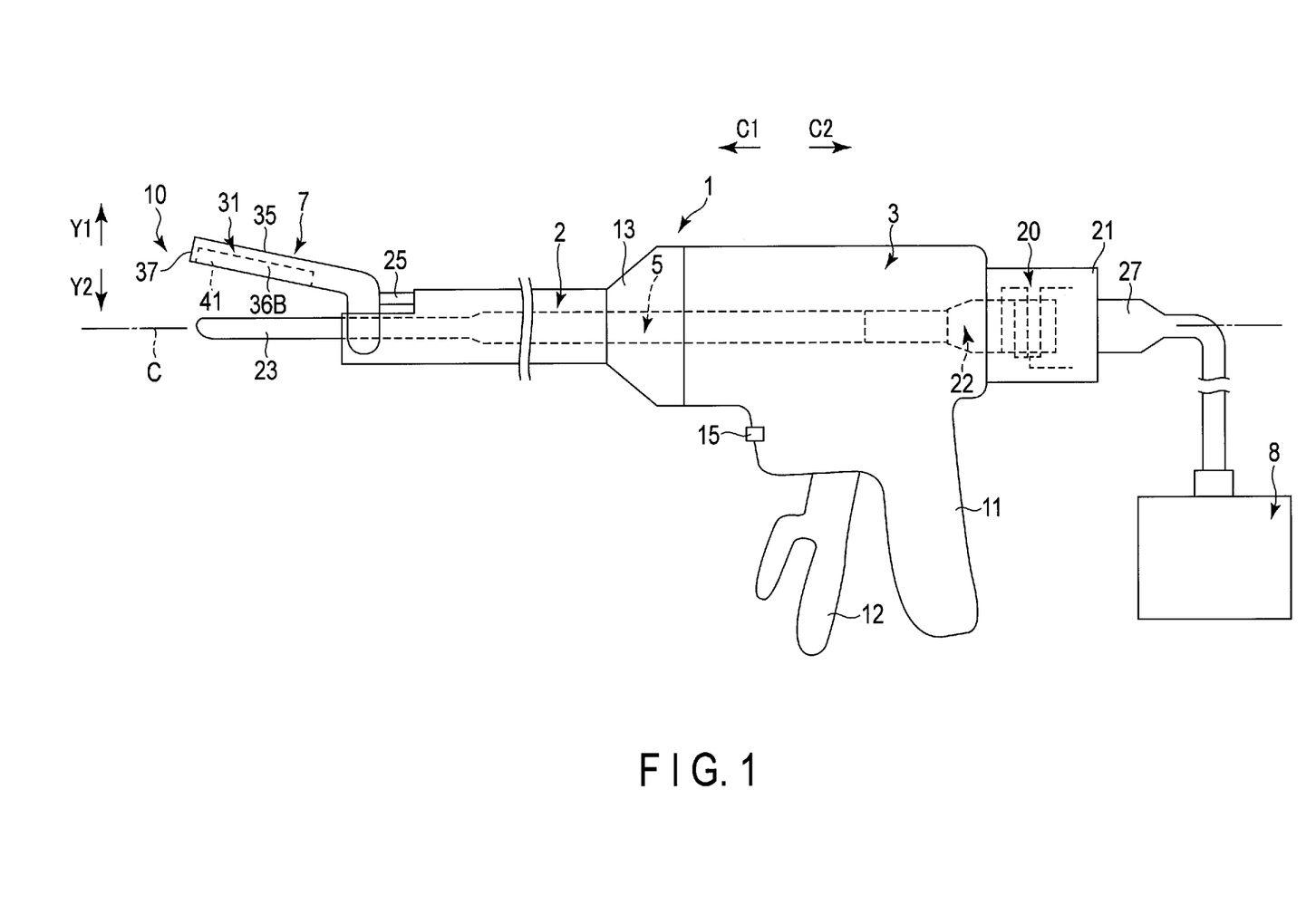
FIG. 1 is a schematic view showing a system in which a treatment instrument according to an exemplary embodiment is used.

An exemplary embodiment will be described with reference to FIGS. 1 to 3. FIG. 1 is a view showing a system in which a treatment instrument 1 according to the present embodiment is used. As shown in FIG. 1, the treatment instrument 1 includes a shaft 2, a housing 3, a rod 5, and a grasping piece 7. The shaft 2 has a substantially linear longitudinal axis C as a central axis. Here, one side in a longitudinal direction along the longitudinal axis C is a distal side (arrow C1 side), and a side opposite to the distal side is a proximal side (arrow C2 side). The housing 3 is connected to a proximal side of the shaft 2 and the shaft 2 extends from the housing 3 toward the distal side. Accordingly, in the shaft 2, a side toward the housing 3 is the proximal side, and a side away from the housing 3 is the distal side.

The housing 3 includes a grip 11 extending along a direction intersecting the longitudinal axis C. In addition, a handle 12 is rotatably attached to the housing 3. As the handle 12 rotates, the handle 12 opens or closes with respect to the grip 11. In the present embodiment, the handle 12 is located on a side on which the grip 11 is located with respect to the longitudinal axis C, and is located on the distal side with respect to the grip 11. In addition, a movement direction of each of an opening movement and a closing movement of the handle 12 is substantially parallel to the longitudinal direction. However, in an embodiment, the handle 12 may be located on the proximal side with respect to the grip 11. In addition, in another embodiment, the handle 12 may be located on a side opposite to the side on which the grip 11 is located with respect to the longitudinal axis C. In this case, the movement direction of each of the opening movement and the closing movement of the handle 12 intersects (is substantially perpendicular to) the longitudinal direction.

A rotation knob 13 is attached to the housing 3. The rotation knob 13 is rotatable with respect to the housing 3 around the longitudinal axis C. In the present embodiment, the rotation knob 13 is attached to the distal side of the housing 3. In addition, the shaft 2 is inserted into an inside of the rotation knob 13 and an inside of the housing 3 from the distal side. In addition, an operation button 15 is attached to the housing 3 as an operation member.

The transducer unit 20 is connected to the housing 3 from the proximal side. In the present embodiment, the transducer unit 20 includes a transducer case 21, and an ultrasonic transducer 22 which is provided inside the transducer case 21. The transducer case 21 is connected to the shaft 2 from the proximal side inside the housing 3. In the present embodiment, the rod 5 extends toward the distal side through the inside of the shaft 2 from the inside of the housing 3. That is, the rod 5 extends from the proximal side toward the distal side in the longitudinal direction. The ultrasonic transducer 22 is connected to the proximal side of the rod 5 inside the housing 3. Moreover, one end of a cable 27 is connected to the transducer case 21. The other end of the cable 27 is connected to an energy source device 8. The energy source device 8 supplies electrical energy to the treatment instrument 1 based on an operation of the operation button 15.

In the present embodiment, the rod 5 is inserted through the shaft 2. In addition, a treating portion (rod treating portion) 23 is provided in the distal portion of the rod 5, and the treating portion 23 protrudes from a distal end of the shaft 2 toward the distal side. Moreover, in an embodiment, the treating portion 23 may extend substantially parallel to the longitudinal axis C of the shaft 2, that is, substantially straight, and in another embodiment, the distal portion of the treating portion 23 may be curved with respect to the longitudinal axis C of the shaft 2. Moreover, in the present embodiment, the rod 5 including the treating portion 23 is formed of a material which has high vibration transmissibility and electrical conductivity, and is formed of a titanium alloy, for example.

The grasping piece (jaw) 7 is rotatably attached to the distal portion of the shaft 2. In addition, the grasping piece 7 extends in a state of facing the treating portion 23 of the rod 5. In the present embodiment, a movable member (movable pipe) 25 extends along the longitudinal axis C inside the shaft 2. In addition, a distal portion of the movable member 25 is connected to the grasping piece 7 and a proximal portion of the movable member 25 is connected to the handle 12 inside the housing 3. The handle 12 is opened or closed to the grip 11, and thus, the movable member 25 moves along the longitudinal axis C. Therefore, the grasping piece 7 rotates, and thus, the grasping piece 7 is opened or closed relative to the treating portion 23. Due to the above-described configuration, in the present embodiment, the grasping piece 7 can open and close to the treating portion 23, and a portion between the grasping piece 7 and the treating portion 23 is openable and closable. In addition, opening and closing directions (directions shown by an arrow Y1 and an arrow Y2) of the grasping piece 7 intersect (are substantially perpendicular to) the extending direction of the treating portion 23 and intersect (are substantially perpendicular to) the longitudinal direction along the longitudinal axis C. Moreover, in the present embodiment, the end effector 10, which treats the treatment target, is formed on the distal portion of the shaft 2 by the treating portion 23 and the grasping piece 7.

Figure 2:
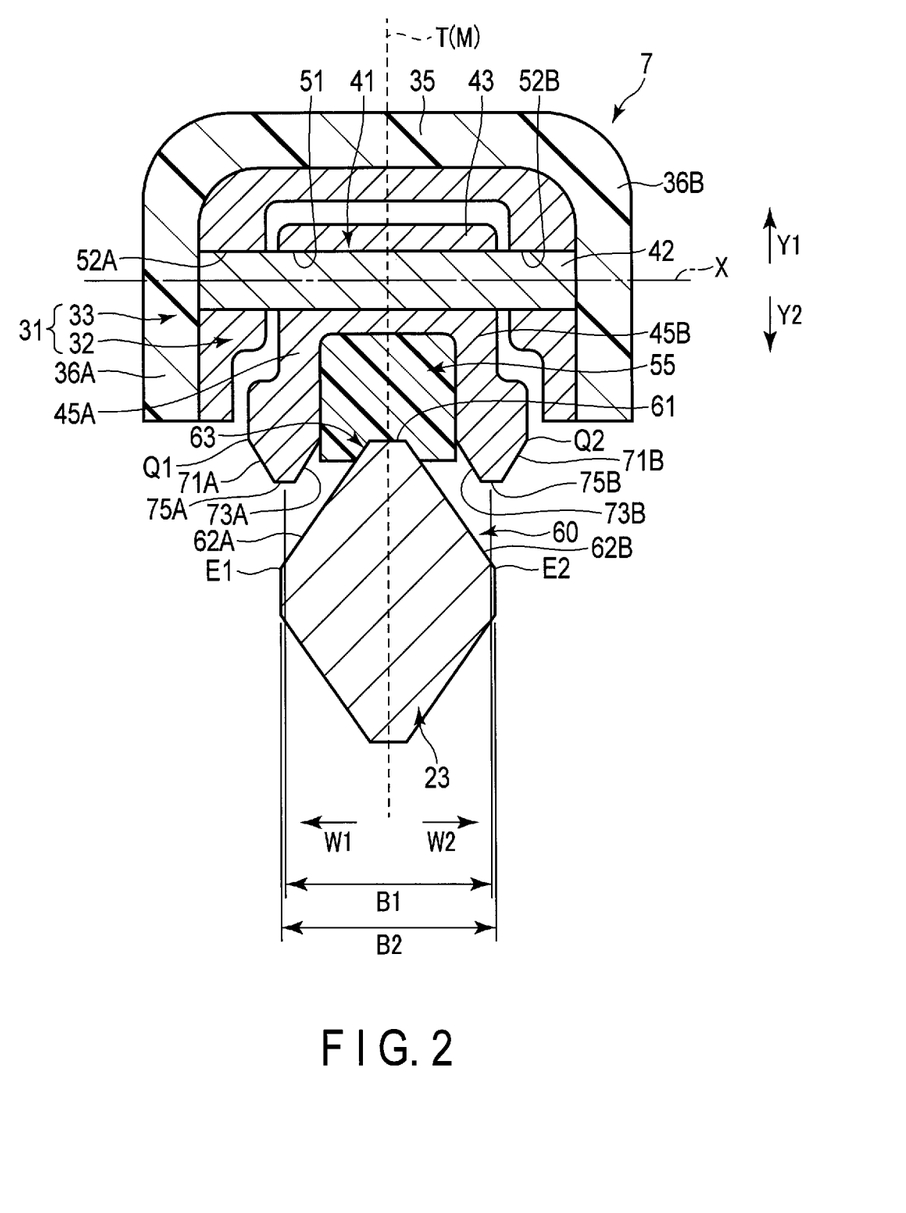
FIG. 2 is a sectional view schematically showing an end effector according to an exemplary embodiment, in a cross section substantially perpendicular to an extending direction of the treating portion.

FIG. 2 is a view showing the end effector 10 in a cross section substantially perpendicular to an extending direction of the treating portion 23. Here, in the embodiment in which the extending direction of the end effector 10 is substantially parallel to the longitudinal axis C, the cross section of FIG. 2 is a cross section which is substantially perpendicular to the longitudinal direction along the longitudinal axis C. In addition, FIG. 2 shows a state in which the treatment target is not disposed between the grasping piece 7 and the treating portion 23 and the grasping piece 7 is closed relative to the treating portion 23. Here, a direction which intersects (is substantially perpendicular to) the extending direction of the treating portion 23 and intersects (is substantially perpendicular to) opening and closing directions of the grasping piece 7 is referred to as a width direction (direction shown by an arrow W1 and an arrow W2) of the end effector 10. In addition, in the opening movement and the closing movement of the grasping piece 7, the grasping piece 7 moves along a motion surface T which is a virtual plane. The motion surface T is substantially parallel to the extending direction of the treating portion 23 and substantially parallel to the opening and closing directions of the grasping piece 7. In addition, the width direction of the end effector 10 intersects (is substantially perpendicular to) the motion surface T. In the present embodiment, for example, the motion surface T is a central surface of the grasping piece 7 passing through a central position M in the width direction of the grasping piece 7 (end effector 10) throughout a range from the proximal end to the distal end of the grasping piece 7. Since the motion surface T is defined as described above, the motion surface T passes through the treating portion 23.

As shown in FIGS. 1 and 2, the grasping piece 7 includes a support 31 attached to the shaft 2. The support body 31 can rotate about an attachment position to the shaft 2. The support body 31 includes a support member 32 formed of a material having electrical conductivity such as a metal, and a cover 33 attached to an outer surface of the support member 32. The cover 33 is formed of a material having electrical insulation such as a resin. The distal portion of the movable member 25 is connected to the support member 32. As described above, the movable member moves along the longitudinal axis C, and thus, the support body 31 rotates about the attachment position to the shaft 2 and the grasping piece 7 opens or closes relative to the treating portion 23. In addition, an electrically insulating coating or the like is applied to a portion of the support member 32 exposed to an outside of the grasping piece 7.

In addition, the support body 31 includes a rear wall 35, side walls 36A and 36B, and a distal wall 37. The distal wall 37 forms a distal end of the grasping piece 7 and forms a portion facing the distal side on the outer surface of the grasping piece 7. Each of the rear wall 35 and the side walls 36A and 36B extends from the distal wall 37 toward the proximal side. In a cross section which passes through the rear wall 35 and the side walls 36A and 36B and is substantially perpendicular to the extending direction of the grasping piece 7, the support body 31 is formed in a substantially U shape. For this reason, the side walls 36A and 36B are disposed to be separated from each other in the width direction. The rear wall 35 forms an end of the grasping piece 7 on a side (arrow Y1 side) where the grasping piece 7 is open, that is, an end of the grasping piece 7 opposite to a side on which the treating portion 23 is located. In addition, the rear wall 35 forms a portion on the outer surface of the grasping piece 17 facing an opening side of the grasping piece 7, that is, a rear surface of the grasping piece 7. In addition, the side wall (first side wall) 36A forms one end of the grasping piece 7 in the width direction, and the side wall (second side wall) 36B forms the other end of the grasping piece 7 in the width direction. In addition, the side wall 36A forms a portion facing one side on the outer surface of the grasping piece 7 in the width direction, that is, one side surface of the grasping piece 7, and the side wall 36B forms a portion facing the other side on the outer surface of the grasping piece 7 in the width direction, that is, the other side surface of the grasping piece 7. In the distal wall 37, the cover 33 is attached to the support member 32 from the distal side. In addition, in the rear wall 35, the cover 33 is attached to the support member 32 from a side where the grasping piece 7 is opened. In addition, in each of the side walls 36A and 36B, the cover 33 is attached to the support member 32 from the outside in the width direction.

Moreover, in the grasping piece 7, an electrode member 41 is attached to the support body 31 via a connection pin 42. Each of the electrode member 41 and the connection pin 42 is formed of a material having electrical conductivity such as a metal. The electrode member 41 is provided on a side on which the treating portion 23 is located with respect to the rear wall 35 of the support body 31, that is, a side to which the grasping piece 7 is closed (arrow Y2 side). Further, the electrode member 41 is provided in an inside of the side walls 36A and 36B of the support body 31 in the width direction and is disposed between the side walls 36A and 36B in the width direction. The electrode member 41 includes a base 43 and side plates 45A and 45B. The rear wall 35 of the support body 31 is provided adjacent to the base 43 of the electrode member 41 on the side where the grasping piece 7 is opened. A gap is formed between the base 43 and the rear wall 35 in opening and closing directions of the grasping piece 7. Each of the side plates 45A and 45B extends from the base 43 toward the side to which the grasping piece 7 is closed. In the cross section substantially perpendicular to the extending direction of the grasping piece 7, the electrode member 41 is formed in a substantially U shape by the base 43 and the side plates 45A and 45B. For this reason, the side plates 45A and 45B are disposed to be separated from each other in the width direction. The side wall 36A of the support body 31 is provided outside and adjacent to the side plate 45A of the electrode member 41 in the width direction, and the side wall 36B of the support body 31 is provided outside and adjacent to the side plate 45B of the electrode member 41 in the width direction. A gap is formed between the side plate 45A and the side wall 36A in the width direction, and a gap is formed between the side plate 45B and the side wall 36B in the width direction.

In the base 43 of the electrode member 41, a hole 51 penetrating the base 43 in the width direction is formed. In addition, a hole 52A is formed along the width direction in the side wall 36A of the support body 31, and a hole 52B is formed along the width direction in the side wall 36B of the support body 31. A connection pin 42 which connects the support body 31 (support member 32) and the electrode member 41 to each other is inserted through the hole 51 and inserted into each of the holes 52A and 52B. The connection pin 42 extends along the width direction in the hole 51 and the holes 52A and 52B. The electrode member 41 can swing (can rotate) with respect to the support body 31 with a central axis of the connection pin 42 as a swinging axis X. That is, the electrode member 41 swings about the swinging axis X which is substantially parallel in the width direction.

When the electrode member 41 swings to one side around the swinging axis X, a portion of the electrode member 41 on the distal side with respect to the swinging axis X approaches the treating portion 23 and moves away from the rear wall 35 of the support body 31. In this case, a portion of the electrode member 41 on the proximal side with respect to the swinging axis X moves away from the treating portion 23 and approaches the rear wall 35. In addition, a portion of the electrode member 41 on the proximal side with respect to the swinging axis X abuts against the rear wall 35, and thus, the swing of the electrode member 41 to one side around the swinging axis X is regulated. Meanwhile, the electrode member 41 swings to the other side around the swinging axis X, and thus, the portion of the electrode member 41 on the distal side with respect to the swinging axis X moves away from the treating portion 23 and approaches the rear wall 35 of the support 31. In this case, the portion of the electrode member 41 on the proximal side with respect to the swinging axis X approaches the treating portion 23 and moves away from the rear wall 35. In addition, the portion of the electrode member 41 on the distal side with respect to the swinging axis X abuts against the rear wall 35, and thus, the swing of the electrode member 41 to the other side around the swinging axis X is regulated. As described above, in the present embodiment, the grasping piece 7 is a seesaw jaw or a wiper jaw in which the electrode member 41 is swingable with respect to the support body 31.

Moreover, in the grasping piece 7, a pad member 55 is fixed to the electrode member 41. The pad member 55 can swing with respect to the support body 31 together with the electrode member 41. For example, the pad member 55 is formed of a resin such as polytetrafluoroethylene (PTFE), and is formed of a material having electrical insulation. The pad member 55 is located on the side on which the treating portion 23 is located with respect to the base 43 of the electrode member 41, that is, the side to which the grasping piece 7 is closed. In addition, the pad member 55 is provided inside the side plates 45A and 45B of the electrode member 41 in the width direction, and is disposed between the side plates 45A and 45B in the width direction.

A rod facing surface 60 facing the grasping piece 7 is provided on the outer surface of the treating portion 23. The rod facing surface 60 faces the side on which the grasping piece 7 is located in the treating portion 23. In addition, in the present embodiment, the rod facing surface extends from one end E1 to the other end E2 of the treating portion 23 in the width direction intersecting (substantially perpendicular to) the motion surface T. Accordingly, the rod facing surface 60 extends inward in the width direction from both ends E1 and E2 of the treating portion 23 in the width direction.

The rod facing surface 60 includes a rod parallel surface 61 which extends to be substantially parallel in the width direction, and rod inclination surfaces 62A and 62B which are inclined relative to the width direction. The central position M of the grasping piece 7 (end effector 10) in the width direction passes through the rod parallel surface 61. The rod inclination surface (first rod inclination surface) 62A extends toward one side (arrow W1 side) in the width direction from the rod parallel surface 61, and the rod inclination surface (second rod inclination surface) 62B extends toward the other side (arrow W2 side) in the width direction from the rod parallel surface 61. In addition, the rod inclination surface (first rod inclination surface) 62A extends inward in the width direction from one end (one end E1 of the treating portion 23) of the rod facing surface 60 in the width direction, and extends up to a boundary between the rod parallel surface 61 and the rod inclination surface 62A. In addition, the rod inclination surface (second rod inclination surface) 62B extends inward in the width direction from the other end (the other end E2 of the treating portion 23) of the rod facing surface 60 in the width direction, and extends to a boundary between the rod parallel surface 61 and the rod inclination surface 62B. Each of the rod inclination surfaces 62A and 62B is inclined in a state where each of the rod inclination surfaces 62A and 62B extends toward the side opposite to the side on which the grasping piece 7 is located as extending outward in the width direction. That is, each of the rod inclination surfaces 62A and 62B extends toward rear surface side of the treating portion 23 as it extends away from the central position M in the width direction.

The grasping piece 7 is closed with respect to the treating portion 23, and thus, the pad member 55 abuts against the rod facing surface 60. That is, an abutment portion 63 against which the pad member 55 abuts is provided on the rod facing surface 60. In the present embodiment, the abutment portion 63 is provided over a range from an inner portion of the rod inclination surface 62A to an inner portion of the rod inclination surface 62B through the rod parallel surface 61 in the width direction. Accordingly, a portion of the rod inclination surface 62A close to the central position M in the width direction and a portion of the rod inclination surface 62B close to the central position M in the width direction become the abutment portion 63 along with the rod parallel surface 61. In the state where the pad member 55 abuts against the abutment portion 63, the support body 31 and the electrode member 41 do not come into contact with the treating portion 23. Accordingly, in the state where the pad member 55 abuts against the abutment portion 63, a gap is formed between the electrode member 41 and the rod facing surface 60.

Electrode inclination surfaces 71A and 71B are provided on an outer surface of the electrode member 41. The electrode inclination surfaces 71A and 71B face the side on which the treating portion 23 is located, that is, the side to which the grasping piece 7 is closed. In the present embodiment, the electrode inclination surface (first electrode inclination surface) 71A is formed on the side plate 45A, and extends inward in the width direction from one end Q1 of the electrode member 41 in the width direction. In addition, the electrode inclination surface (second electrode inclination surface) 71B is formed on the side plate 45B, and extends inward in the width direction from the other end Q2 of the electrode member 41 in the width direction. In addition, the electrode inclination surface (first electrode inclination surface) 71A is provided on a side on which the rod inclination surface (first rod inclination surface) 62A is located with respect to the central position M in the width direction, and the electrode inclination surface (second electrode inclination surface) 71B is provided on a side on which the rod inclination surface (second rod inclination surface) 62B is located with respect to the central position M in the width direction. Each of the electrode inclination surfaces 71A and 71B is inclined in a state where each of the electrode inclination surfaces 71A and 71B extends toward the side opposite to the side on which the treating portion 23 is located as extending outward in the width direction. That is, each of the electrode inclination surfaces 71A and 71B extends the side on which the grasping piece 7 is opened as it extends away from the central position M in the width direction.

In addition, the electrode inclination surface 71A is provided inside and adjacent to the side wall 36A of the support 31 in the width direction. In addition, in any state within a range in which the electrode member 41 can swing, a portion or the entire portion of the electrode inclination surface 71A protrudes to the side on which the treating portion 23 is located, with respect to the side wall 36A, that is, the side to which the grasping piece 7 is closed. Similarly, the electrode inclination surface 71B is provided inside and adjacent to the side wall 36B of the support 31 in the width direction. In addition, in any state within the range in which the electrode member 41 can swing, a portion or the entire portion of the electrode inclination surface 71B protrudes to the side on which the treating portion 23 is located, with respect to the side wall 36B, that is, the side to which the grasping piece 7 is closed.

Electrode facing surfaces 73A and 73B facing the rod facing surface 60 are provided on the outer surface of the electrode member 41. The electrode facing surfaces 73A and 73B face the side on which the treating portion 23 is located, that is, the side to which the grasping piece 7 is closed. In the present embodiment, the electrode facing surface (first electrode facing surface) 73A is formed on the side plate 45A and faces the rod inclination surface (first rod inclination surface) 62A. In addition, the electrode facing surface 73A is provided inside the electrode inclination surface (first electrode inclination surface) 71A in the width direction, and is disposed between the electrode inclination surface 71A and the pad member 55 in the width direction. Moreover, the electrode facing surface (second electrode facing surface) 73B is formed on the side plate 45B and faces the rod inclination surface (second rod inclination surface) 62B. In addition, the electrode facing surface 73B is provided inside the electrode inclination surface (second electrode inclination surface) 71B in the width direction, and is disposed between the electrode inclination surface 71B and the pad member 55 in the width direction.

According to this configuration, the pad member 55 is provided between the electrode facing surfaces 73A and 73B in the width direction. In addition, the abutment portion 63 of the rod facing surface 60 abutting against the pad member 55 is located between the electrode facing surfaces 73A and 73B in the width direction. Accordingly, the central position M of the grasping piece 7 (end effector 10) in the width direction passes through the pad member 55 and the abutment portion 63. Each of the electrode facing surfaces 73A and 73B is inclined in a state where each of the electrode facing surface 73A and 73B extends the side on which the treating portion 23 is located as extending outward in the width direction. That is, each of the electrode facing surfaces 73A and 73B extends the side to which the grasping piece 7 is closed as it extends away from the central position M in the width direction.

An apex (first apex) 75A whose outer surface protrudes toward the side on which the treating portion 23 is located is provided on the side plate 45A of the electrode member 41, and an apex (second apex) 75B whose outer surface protrudes toward the side on which the treating portion 23 is located is provided on the side plate 45B of the electrode member 41. The apex 75A is provided between the electrode inclination surface (first electrode inclination surface) 71A and the electrode facing surface (first electrode facing surface) 73A in the width direction, and the apex 75B is provided between the electrode inclination surface (second electrode inclination surface) 71B and the electrode facing surface (second electrode facing surface) 73B in the width direction. In addition, a distance between the electrode inclination surface (first electrode inclination surface) 71A and the electrode facing surface (first electrode facing surface) 73A in the width direction decreases as it approaches the apex (first apex) 75A, that is, decreases toward the side on which the treating portion 23 is located. Similarly, a distance between the electrode inclination surface (second electrode inclination surface) 71B and the electrode facing surface (second electrode facing surface) 73B in the width direction decreases as it approaches the apex (second apex) 75B, that is, decreases toward the side on which the treating portion 23 is located.

In addition, each of the rod inclination surfaces 62A and 62B and the abutment portion 63 shown in cross section of FIG. 2 continuously extends from the proximal portion to the distal portion in the treating portion 23. Moreover, each of the side walls 36A and 36B, the pad member 55, the electrode inclination surfaces 71A and 71B, the electrode facing surfaces 73A and 73B, and the apexes 75A and 75B shown in a cross section in FIG. 2 continuously extends from the proximal portion to the distal portion in the grasping piece 7. That is, in most of a range from the proximal portion to the distal portion in the end effector 10, the cross section substantially perpendicular to the extending direction of the treating portion 23 has the same configuration as that of FIG. 2 except whether or not the connection pin 42 is provided.

In addition, a first distance B1 between the apexes 75A and 75B in the width direction and a second distance B2 from one end (E1) to the other end (E2) of the rod facing surface 60 in the width direction are defined. In an embodiment, the first distance B1 is the same as the second distance B2. In another embodiment, the first distance B1 is longer than the second distance B2, and in still another embodiment, the first distance B1 is shorter than the second distance B2. Accordingly, the first distance B1 may be equal to or longer than the second distance B2 or may be shorter than the second distance B2.

Next, function and effects of the treatment instrument 1 of the present embodiment will be described. When a treatment is performed using the treatment instrument 1, an operator inserts the end effector 10 into a body cavity such as an abdominal cavity. In addition, a treatment target such as a living tissue (for example, a blood vessel) is placed between the treating portion 23 and the grasping piece 7, and the handle 12 is closed to the grip 11. Accordingly, the grasping piece 7 is closed relative to the treating portion 23, and the treatment target is grasped between the grasping piece 7 and the treating portion 23. In this state, the operator presses the operation button 15. Based on an operation input by the operation button 15, the energy source device 8 outputs electrical energy. In this case, alternating current electric power of any frequency within a predetermined frequency range is supplied as the electrical energy from the energy source device 8 to the ultrasonic transducer 22. Accordingly, ultrasonic vibrations are generated by the ultrasonic transducer 22. The generated ultrasonic vibrations are transmitted from the proximal side to the distal side in the rod 5 and are transmitted to the treating portion 23. In a state where the rod 5 transmits the ultrasonic vibrations, the rod 5 including the treating portion 23 vibrates at any frequency within a predetermined frequency range. The ultrasonic vibrations transmitted to the treating portion 23 are applied to the grasped treatment target as the treatment energy. In this case, frictional heat is generated between the treating portion 23 and the treatment target, and the treatment target is cut simultaneously with coagulation by the frictional heat.

In a state where the electrical energy is output from the energy source device 8, the high frequency electric power is supplied from the energy source device 8 to the electrode member 41 of the grasping piece 7 and the treating portion 23 as the electrical energy. In this case, the high frequency electric power is supplied to the treating portion 23 via an electrical wire (not shown) inside the cable 27, the rod 5, or the like, and the high frequency electric power is supplied to the electrode member 41 via the electrical wire (not shown) inside the cable 27, an electrically conductive portion (not shown) of the transducer case 21, the movable member 25, and the support member 32. By supplying the high frequency electric power to the electrode member 41 and the treating portion 23, the electrode member 41 and the treating portion 23 function as electrodes having electric potentials different from each other. As described above, the electrode member 41 and the treating portion 23 function as the electrodes, and thus, the high frequency current flows through the treatment target grasped between the electrode member 41 and the treating portion 23, and the high frequency current is applied to the treatment target as treatment energy. In this case, the treatment target is denatured by heat caused by the high frequency current, and the coagulation of the treatment target is promoted. That is, a blood vessel or the like which is the treatment target is gelatinized and joined by the heat caused by the high frequency current, and is sealed.

In addition, in a state where the electrical energy is output from the energy source device 8, a processing unit (not shown) such as a processor provided in the energy source device 8 detects an output current and an output voltage according to the electrical energy (high frequency electric power) supplied to the treating portion 23 and the electrode member 41. Moreover, based on detection results of the output current and the output voltage, the processing unit detects an impedance of a circuit through which the high frequency current flows, and detects an impedance of the treatment target (living tissue). In a state where the electrical energy is output from the energy source device 8, when some time passes after an application of the high frequency current to the treatment target starts, water in the treatment target decreases with time, and the impedance of the treatment target increases with time. For example, based on that the impedance of the treatment target is equal to or more than a predetermined threshold, the processing unit stops the supply of the electrical energy from the energy source device 8 to the treating portion 23 and the electrode member 41. As a result, the high frequency current is not applied to the treatment target.

Here, in the treatment using the high frequency current, the treatment target is appropriately gelatinized and joined by the high frequency current in a case where the impedance of the treatment target is within a predetermined range. For example, the above-described predetermined threshold is a predefined value, which is larger than an upper limit value of the above-described predetermined range in which the treatment target is appropriately gelatinized and joined. In addition, in an embodiment, a supply of the electrical energy (alternating current electric power) from the energy source device 8 to the ultrasonic transducer 22 may be stopped at the same time as a supply of the electrical energy from the energy source device 8 to the treating portion 23 and the electrode member 41 is stopped. By stopping the supply of the electrical energy to the ultrasonic transducer 22, ultrasonic vibrations are not generated by the ultrasonic transducer 22.

Figure 3:
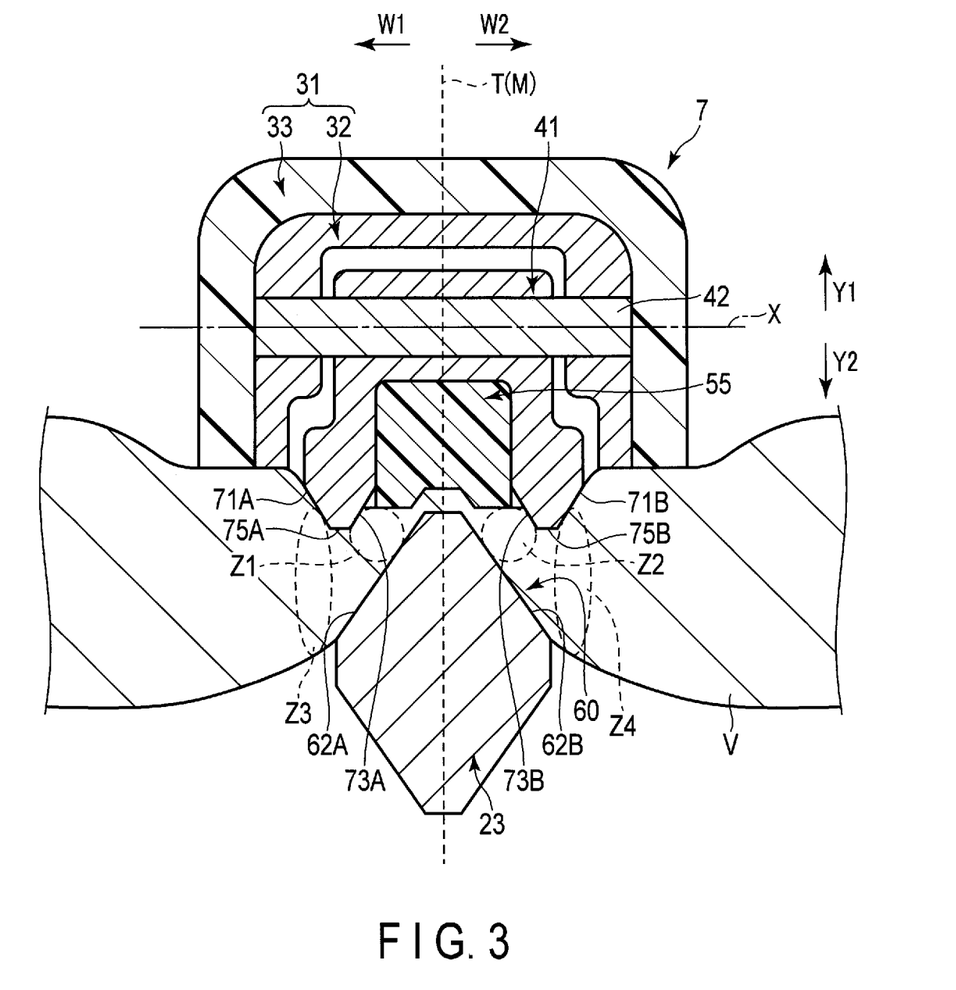
FIG. 3 is a sectional view of a cross section substantially perpendicular to the extending direction of the treating portion schematically showing a state where a treatment target is grasped between the treating portion and a grasping piece according to an exemplary embodiment.

FIG. 3 is a view schematically showing a state where a treatment target V is grasped between the treating portion 23 and the grasping piece 7, in the cross section substantially perpendicular to the extending direction of the treating portion 23. As shown in FIG. 3, in the state where the treatment target V is grasped between the treating portion 23 and the grasping piece 7, in the treatment target V, a region Z1 is in contact with the electrode facing surface 73A and a region Z2 is in contact with the electrode facing surface 73B. In addition, in the treatment target V, a region Z3 located outside the region Z1 in the width direction is in contact with the electrode inclination surface 71A, and a region Z4 located outside the region Z2 in the width direction is in contact with the electrode inclination surface 71B. Here, in the state where the treatment target V is grasped between the treating portion 23 and the grasping piece 7, a gap between the electrode facing surface 73A and the rod inclination surface 62A facing each other is small. Accordingly, the region Z1 which is in contact with the electrode facing surface 73A is sandwiched between the electrode facing surface 73A and the rod inclination surface 62A at a high pressure, and is compressed by a high pressure. Similarly, the region Z2 which is in contact with the electrode facing surface 73B is sandwiched between the electrode facing surface 73B and the rod inclination surface 62B at a high pressure, and is compressed by a high pressure.

In addition, in the present embodiment, each of the electrode inclination surfaces 71A and 71B is inclined in a state where each of the electrode inclination surfaces 71A and 71B extends the side opposite to the side on which the treating portion 23 is located as extending outward in the width direction. Accordingly, in the state where the treatment target V is grasped between the treating portion 23 and the grasping piece 7, the electrode inclination surface 71A does not face the rod inclination surface 62A, and a distance from the treating portion 23 to the electrode inclination surface 71A is large. Accordingly, in the treatment target V, the region Z3 which is in contact with the electrode inclination surface 71A is not compressed at a pressure higher than that of the region Z1. Similarly, in the treatment target V, the region Z4 which is in contact with the electrode inclination surface 71B is not compressed at a pressure higher than that of the region Z2. In addition, in the state where the ultrasonic vibrations are applied to the treatment target V as described above, the treatment target V is cut at a portion between the regions Z1 and Z2 in the width direction, that is, at a portion sandwiched between the pad member 55 and the abutment portion 63.

In the present embodiment, the grasped treatment target V is in contact with the electrode member 41 in the regions Z3 and Z4 not compressed at a high pressure in addition to the regions Z1 and Z2 compressed at a high pressure. Accordingly, in the state where the high frequency current is applied to the treatment target V as the treatment energy, the high frequency current flows to the regions Z3 and Z4 in addition to the regions Z1 and Z2. Here, if the treatment target V is cauterized in the regions Z1 and Z2 by the heat caused by the high frequency current, the impedances of the regions Z1 and Z2 increase, and the high frequency current does not easily flow to the regions Z1 and Z2. In the present embodiment, even if the high frequency current does not easily flow to the regions Z1 and Z2, the high frequency current flows through the regions Z3 and Z4 which are not compressed at a high pressure. Therefore, even if the high frequency current does not easily flow to the regions Z1 and Z2, a path through which the high frequency current flows between the treating portion 23 and the electrode member 41 is secured, and thus, the impedance of the treatment target (living tissue) V is prevented from rapidly increasing.

As described above, when some time passes after the application of the high frequency current to the treatment target V starts, the impedance of the treatment target V increases with time. As described above, by preventing the rapid increase of the impedance, a time until the impedance exceeds the above-described predetermined range in which the treatment target V is appropriately gelatinized and joined is lengthened. That is, the time for which the high frequency current is applied to the treatment target V in a state in which the impedance is within the predetermined range (a state in which the impedance remains at or below the upper limit of the predetermined range) is lengthened. Accordingly, a time when the treatment target V is appropriately gelatinized and joined by the heat caused by the high frequency current is lengthened. As a result, the treatment target V is appropriately coagulated and sealed, and appropriate treatment performance is exhibited in the treatment using the high frequency current.

In addition, the rapid increase in the impedance is prevented, the time until the impedance exceeds the above-described predetermined range in which the treatment target V is appropriately gelatinized and joined is lengthened, and thus, the time until the impedance of the treatment target V is equal to or more than the above-described predetermined threshold is lengthened. That is, a time from the start of the supply of the electrical energy to an automatic stop of the supply of the electrical energy from the energy source device 8 to the treating portion 23 and the electrode member 41 is lengthened. As a result, a sufficient amount of high frequency current is applied as the treatment energy for the coagulation and sealing of the treatment target V, and the treatment performance in the treatment using the high frequency current is improved.

Moreover, as in the present embodiment, in the configuration in which the side walls 36A and 36B of the support body 31 are provided outside the electrode member 41 in the width direction, dimensions of the electrode member 41 in the width direction decrease, and a contact area between the treatment target V and the electrode member 41 decreases. In this case, even if the high frequency current does not easily flow to the regions Z1 and Z2 compressed at a high pressure, as described above, the high frequency current flows through the regions Z3 and Z4 which are not compressed at a high pressure. Therefore, even if the high frequency current does not easily flow to the regions Z1 and Z2, the path through which the high frequency current flows between the treating portion 23 and the electrode member 41 is secured, and thus, the impedance of the treatment target (living tissue) V is prevented from rapidly increasing. That is, even in the configuration in which the dimensions of the electrode member 41 in the width direction is small, the impedance of the treatment target V is prevented from rapidly increasing.

In addition, in the present embodiment, as described above, the side walls 36A and 36B of the support body 31 are provided outside the electrode member 41 in the width direction. Therefore, the dimensions of the electrode member 41 in the width direction, that is, a distance between both ends Q1 and Q2 of the electrode member 41 in the width direction, can be shorter than a distance between the side walls 36A and 36B. Since the dimensions of the electrode member 41 in the width direction decrease, in the treatment target (living tissue) V, a range in which the high frequency current flows to a portion outside the end effector 10 (treating portion 23 and grasping piece 7) in the width direction decreases. Accordingly, in the treatment target V, an invasion range of the heat caused by the high frequency current decreases in the portion outside the end effector 10 in the width direction. That is, in the treatment target V, a lateral invasion of the heat caused by the high frequency current, that is, an outward invasion in the width direction decreases. For example, in the treatment target V, the invasion of the heat caused by the high frequency current decreases in the portion outside the regions Z3 and Z4 in the width direction. The lateral invasion of the heat caused by the high frequency current decreases, and thus, treatment performance is improved in the treatment using the high frequency current.

In addition, in the present embodiment, at least a part of the electrode inclination surface 71A protrudes to the side on which the treating portion 23 is located with respect to the side wall 36A, and at least a part of the electrode inclination surface 71B protrudes to the side on which the treating portion 23 is located with respect to the side wall 36B. For this reason, even in the configuration in which the side walls 36A and 36B are provided, the grasped treatment target V comes into contact with the electrode inclination surfaces 71A and 71B. That is, even in the configuration in which the side walls 36A and 36B are provided, the regions Z3 and Z4 which come into contact with the electrode member 41 without being compressed at a high pressure are formed in the treatment target V. Accordingly, even in the configuration in which the side walls 36A and 36B are provided, as described above, the impedance of the treatment target V is prevented from rapidly increasing.

Moreover, in an embodiment of the present embodiment, as described above, the first distance B1 between the apexes 75A and 75B in the width direction is larger than the second distance B2 from the one end (E1) of the rod facing surface 60 in the width direction to the other end (E2) thereof. In this case, both ends E1 and E2 of the treating portion 23 approach the central position M in the width direction, and thus, in the treatment target V, the range in which the high frequency current flows to the portion outside the end effector 10 in the width direction decreases. Accordingly, in the treatment target V, the lateral invasion of the heat caused by the high frequency current further decreases.

Meanwhile, in still another embodiment, as described above, the first distance B1 is shorter than the second distance B2. In this case, in the treatment target V, the contact area between the treating portion 23 and the rod facing surface 60 increases. Accordingly, in the treatment target V, in the state where the high frequency current does not easily flow to the regions Z1 and Z2 compressed at a high pressure, the high frequency current more easily flows to the regions Z3 and Z4 not compressed at a high pressure. Accordingly, the rapid increase of the impedance of the treatment target V is more effectively prevented, and the treatment performance is further improved in the treatment using the high frequency current.

In addition, in the above exemplary embodiment, each of the electrode inclination surfaces 71A and 71B, the electrode facing surfaces 73A and 73B, and the apexes 75A and 75B shown in the cross section of FIG. 2 continuously extends from the proximal portion to the distal portion in the grasping piece 7. However, it is not limited to this. For example, in an exemplary embodiment shown in FIGS. 4 and 5, an end portion of a side plate 45A of an electrode member 41 on a side on which a treating portion 23 is located is formed unevenly along an extending direction of a grasping piece 7. That is, in the end portion of the side plate 45A on the side on which the treating portion 23 is located, protrusion 81A protruding to the side on which the treating portion 23 is located and recesses 82A recessed to the side opposite to the side on which the treating portion 23 is located are alternately juxtaposed in the extending direction (longitudinal direction) of the grasping piece 7. Similarly, an end portion of a side plate 45B of the electrode member 41 on the side on which the treating portion 23 is located is formed unevenly in the extending direction of the grasping piece 7. That is, in the end portion of the side plate 45B on the side on which the treating portion 23 is located, protrusion 81B protruding to the side on which the treating portion 23 is located and recesses 82B recessed to the side opposite to the side on which the treating portion 23 is located are alternately juxtaposed in the extending direction (longitudinal direction) of the grasping piece 7.

In the present modification, an electrode inclination surface 71A, an electrode facing surface 73A, and an apex 75A are formed only in the protrusion 81A and are not formed in the recess 82A. Similarly, an electrode inclination surface 71B, an electrode facing surface 73B, and an apex 75B are formed only in the protrusion 81B and are not formed in the recess 82B. Accordingly, in the present modification, a cross section which is substantially perpendicular to the extending direction of the grasping piece 7 and passes through the protrusions 81A and 81B has the electrode inclination surfaces 71A and 71B, the electrode facing surfaces 73A and 73B, and the apexes 75A and 75B, and has the same cross section as that shown in FIG. 2. However, in a cross section shown in FIG. 5 which is substantially perpendicular to the extending direction of the grasping piece 7 and passes through the recesses 82A and 82B, the electrode inclination surfaces 71A and 71B, the electrode facing surfaces 73A and 73B, and the apexes 75A and 75B are not formed.

Figure 4:
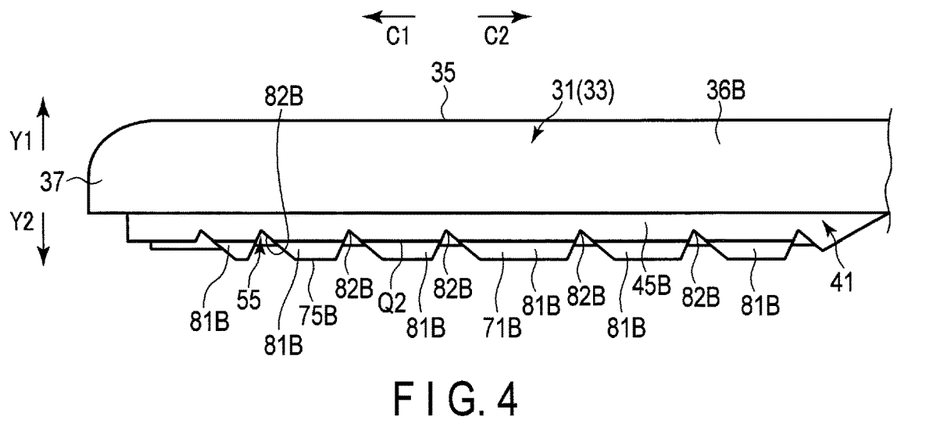
FIG. 4 is a schematic view showing a state when a grasping piece according to an exemplary embodiment is viewed from one side in a width direction.
Figure 5:
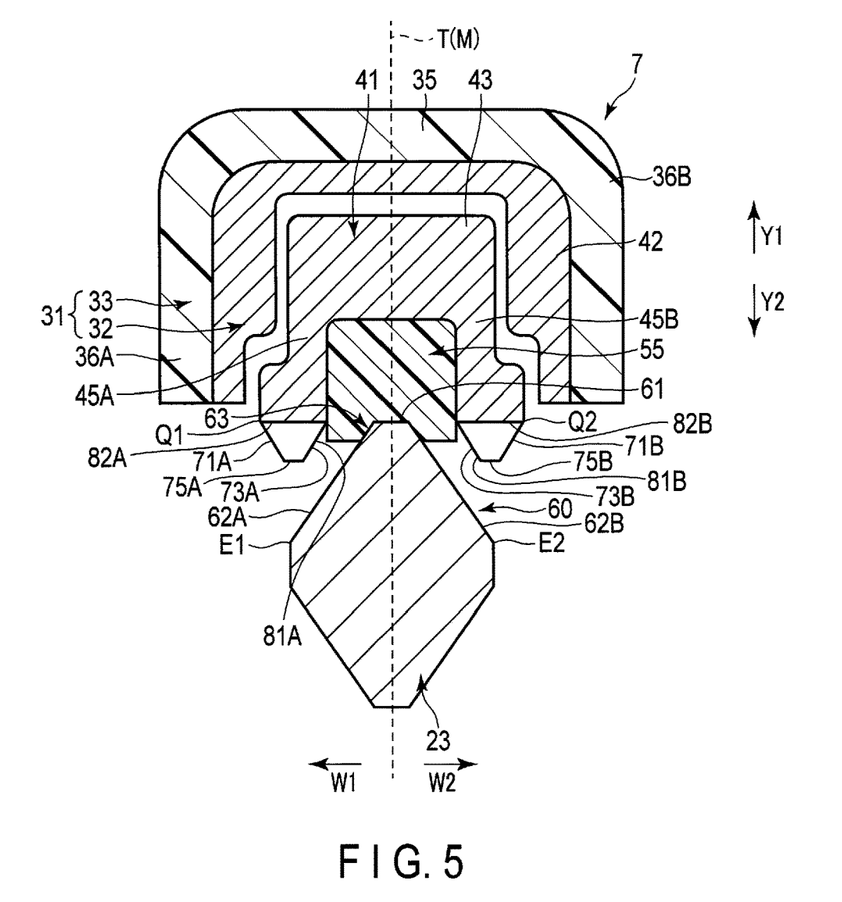
FIG. 5 is a sectional view schematically showing an end effector in the cross section substantially perpendicular to the extending direction of the treating portion.

In addition, in the present modification, in any state within a range in which the electrode member 41 can swing, each of bottom portions of the recesses 82A is located on the side on which the treating portion 23 is located with respect to the side wall 36A of the support body 31. That is, each of the bottom portions of the recesses 82A protrudes from the side wall 36A to the side on which the treating portion 23 is located. Similarly, in any state within the range in which the electrode member 41 can swing, each of bottom portions of the recesses 82B is located on the side on which the treating portion 23 is located with respect to the side wall 36B of the support body 31. That is, each of the bottom portions of the recesses 82B protrudes from the side wall 36B to the side on which the treating portion 23 is located.

According to the above-described configuration, in the present modification, the treatment target grasped between the treating portion 23 and the grasping piece 7 enters each of the recesses 82A and 82B. Accordingly, the grasped treatment target is prevented from moving in the extending direction (longitudinal direction) of the grasping piece 7. That is, the grasped treatment target is prevented from being shifted to a distal side and a proximal side.

In the above-described embodiment or the like, the treatment instrument (1) includes the rod (5) which extends from the proximal side to the distal side in the longitudinal direction and transmits the ultrasonic vibrations from the proximal side to the distal side, and the treating portion (23) having electrical conductivity is provided in the distal portion of the rod (5). The grasping piece (7) is openable and closable relative to the treating portion (23), and the motion surface (T) in the opening movement and the closing movement of the grasping piece (7) passes through the treating portion (23). The rod facing surface (60) facing the grasping piece (7) is provided on the outer surface of the treating portion (23), and the rod facing surface (60) extends inward in the width direction from the end (E1, E2) of the treating portion (23) in the width direction intersecting the motion surface (T). The grasping piece (7) includes the electrode member (41) having electrical conductivity, the electrode inclination surface (71A, 71B) facing the side on which the treating portion (23) is located is provided on the outer surface of the electrode member (41). The electrode inclination surface (71A, 71B) is inclined in a state which the electrode inclination surface extends the side opposite to the side on which the treating portion (23) is located as extending outward in the width direction.

Additional advantages and modifications will readily occur to those skilled in the art. Therefore, the present disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment instrument comprising:
a rod that extends from a proximal side to a distal side in an extending direction, and includes, on the distal side, a treatment portion having electrical conductivity; and
a grasping piece that is openable and closable relative to the treatment portion, and includes an electrode member having electrical conductivity,
wherein:
the treatment instrument extends in: a longitudinal direction along the extending direction of the rod, a width direction orthogonal to the longitudinal direction, and a height direction that extends from a treatment portion side to a grasping piece side, the longitudinal direction and the height direction being orthogonal to each other and defining a virtual plane that is orthogonal to the width direction,
the treatment portion includes a rod outer surface that faces the grasping piece,
the rod outer surface includes:
a first rod inclination surface that is inclined with respect to the virtual plane so as to extend from a first end to a second end in a direction moving: (i) towards the grasping piece side in the height direction and (ii) inward in the width direction, the first end being on an outer side of the second end in the width direction, and the second end being closer to the grasping piece side in the height direction than the first end is to the grasping piece side in the height direction,
a second rod inclination surface that is inclined with respect to the virtual plane so as to extend from a first end to a second end in the direction moving: (i) towards the grasping piece side in the height direction and (ii) inward in the width direction, the first end being on an outer side of the second end in the width direction, and the second end being closer to the grasping piece side in the height direction than the first end is to the grasping piece side in the height direction, and
a rod intermediate surface that is provided between the first rod inclination surface and the second rod inclination surface in the width direction, and extends in the width direction,
the electrode member includes:
an electrode inclination surface that faces a side on which the treatment portion is located, and is inclined with respect to the virtual plane, the electrode inclination surface including:
a first electrode inclination surface provided on a side on which the first rod inclination surface is located with respect to a central position in the width direction, the first electrode inclination surface extending from a first end to a second end in a direction moving: (i) away from the treatment portion side in the height direction and (ii) outward in the width direction, the first end being on an inner side of the second end in the width direction, and being closer to the treatment portion side in the height direction than the second end is to the treatment portion side in the height direction, and
a second electrode inclination surface provided on a side on which the second rod inclination surface is located with respect to the central position in the width direction, the second electrode inclination surface extending from a first end to a second end in the direction moving (i) away from the treatment portion side in the height direction, and (ii) outward in the width direction, the first end being on an inner side of the second end in the width direction, and being closer to the treatment portion side in the height direction than the second end is to the treatment portion side in the height direction,
an electrode facing surface that is disposed between the first electrode inclination surface and the second electrode inclination surface in the width direction, and is inclined with respect to the virtual plane so as to extend from a first end to a second end in a direction moving: (i) towards the treatment portion side in the height direction and (ii) outward in the width direction, the first end being on an inner side of the second end in the width direction, and the second end being closer to the treatment portion side in the height direction than the first end is to the treatment portion side in the height direction, the electrode facing surface including:
a first electrode facing surface that faces the first rod inclination surface, and
a second electrode facing surface that faces the second rod inclination surface,
a first apex that is provided between the first electrode inclination surface and the first electrode facing surface in the width direction and faces the first rod inclination surface, and
a second apex that is provided between the second electrode inclination surface and the second electrode facing surface in the width direction and faces the second rod inclination surface, the first apex and the second apex each being a planar surface that extends along the width direction,
a first distance between the first apex and the second apex in the width direction is shorter than a second distance from the first end of the first rod inclination surface of the treatment portion to the first end of the second rod inclination surface of the treatment portion in the width direction,
the grasping piece includes a pad member that is provided between the first electrode facing surface and the second electrode facing surface in the width direction, and has electrical insulation, and
the pad member includes a pad abutment surface that abuts against the rod intermediate surface, and extends along the width direction.

2. The treatment instrument according to claim 1, wherein:
the grasping piece further includes a support body that supports the electrode member,
the support body includes a side wall that is provided outside and adjacent to the electrode member in the width direction, and
a part or an entirety of the electrode inclination surface protrudes from the side wall in a direction toward the treatment portion.

3. The treatment instrument according to claim 1, wherein in a state where a living tissue is grasped between the grasping piece and the treatment portion, a first region of the living tissue grasped between the first and second electrode facing surfaces and the first and second rod inclination surfaces is compressed at a high pressure compared to a second region of the living tissue that is in contact with the electrode inclination surface.

4. The treatment instrument according to claim 1, wherein in a state where a living tissue is grasped between the grasping piece and the treatment portion, a distance between the first and second electrode facing surface and the first and second rod inclination surfaces, respectively, is shorter than a distance between the first and second electrode inclination surface and the first and second rod inclination surfaces, respectively.

5. The treatment instrument according to claim 1, wherein the grasping piece is configured to move in a direction along the virtual plane.

6. The treatment instrument according to claim 5, wherein the virtual plane passes through a central position in the width direction of the grasping piece.

7. The treatment instrument according to claim 1, wherein:
the electrode member includes a base member and first and second side plates extending from the base member;
the first and second side plates are separated from each other in the width direction such that the pad member is disposed between the side plates; and
the first electrode inclination surface and the first electrode facing surface are disposed on the first side plate, and the second electrode inclination surface and the second electrode facing surface are disposed on the second side plate.

8. The treatment instrument according to claim 1, wherein when the grasping piece is closed relative to the treatment portion, each of the first electrode facing surface and a part of the first apex is opposed to the first rod inclination surface and each of the second electrode facing surface and a part of the second apex is opposed to the second rod inclination surface.

9. The treatment instrument according to claim 1, wherein the second end of the first electrode facing surface and the first end of the first electrode inclination surface define the first apex,
a third distance is defined between the first end of the first electrode inclination surface and the first rod inclination surface in the height direction, and a fourth distance is defined between the second end of the first electrode facing surface and the first rod inclination surface in the height direction, and
the third distance is larger than the fourth distance.

10. The treatment instrument according to claim 1, wherein
the first rod inclination surface is inclined less than 90° with respect to the virtual plane, and
the second rod inclination surface is inclined less than 90° with respect to the virtual plane.

11. The treatment instrument according to claim 1, wherein
the rod intermediate surface is provided between the first apex and the second apex in the width direction.

12. A treatment instrument comprising:
a rod that extends from a proximal side to a distal side in a longitudinal direction, and includes, on the distal side, a treatment portion having electrical conductivity;
a grasping piece that is openable and closable relative to the treatment portion, and includes an electrode member having electrical conductivity, the grasping piece being configured to move in a direction along a virtual plane that extends along an extending direction of the treatment portion and along opening and closing directions of the grasping piece; and
an energy source device configured to supply high frequency electric power to the electrode member and the treatment portion,
wherein:
the treatment portion includes a rod outer surface that faces the grasping piece;
the electrode member includes a first electrode portion, a second electrode portion, a first apex, and a second apex, the second electrode portion being provided outside the first electrode portion in a width direction that intersects the virtual plane;
the first electrode portion includes a first electrode facing surface and a second electrode facing surface that are provided on opposite sides of the virtual plane in the width direction;

the second electrode portion includes a first electrode inclination surface and a second electrode inclination surface that are provided on opposite sides of the virtual plane in the width direction;

the first apex is provided between the first electrode inclination surface and the first electrode facing surface in the width direction and faces the rod outer surface;

the second apex is provided between the second electrode inclination surface and the second electrode facing surface in the width direction and faces the rod outer surface;

each of the first apex and the second apex is a planar surface that extends along the width direction;

a distance between the first apex and the second apex in the width direction is shorter than a width of a widest portion of the treatment portion in the width direction;

the treatment instrument is configured to:

flow a high frequency current to a portion between the rod outer surface of the treatment portion and the first electrode portion, and compress a living tissue at a first pressure between the rod outer surface of the treatment portion and the first electrode portion in a state where the living tissue is grasped between the grasping piece and the treatment portion, and flow a high frequency current to a portion between the rod outer surface of the treatment portion and the second electrode portion, and compress the living tissue by the second electrode portion at a second pressure smaller than the first pressure in the state where the living tissue is grasped between the grasping piece and the treatment portion; and a first distance between the rod outer surface of the treatment portion and the first electrode portion in the state where the living tissue is grasped between the grasping piece and the treatment portion is smaller than a second distance between the rod outer surface of the treatment portion and the second electrode portion in the state where the living tissue is grasped between the grasping piece and the treatment portion.

13. The treatment instrument according to claim 12, wherein the first electrode inclination surface and the second electrode inclination surface are inclined with respect to the virtual plane so as to extend from a first end to a second end in a direction moving: (i) away from a side of the treatment portion in a height direction extending along the opening and closing directions and (ii) outward in the width direction, the first end being on an inner side of the second end in the width direction, and being closer to the side of the treatment portion in the height direction than the second end is to the side of the treatment portion in the height direction.

14. The treatment instrument according to claim 12, wherein
an end of the first electrode facing surface and an end of the first electrode inclination surface define the first apex,
a third distance is defined between the end of the first electrode inclination surface and the rod outer surface in the opening and closing directions, and a fourth distance is defined between the end of the first electrode facing surface and the rod outer surface in the opening and closing directions, and
the third distance is larger than the fourth distance.

15. The treatment instrument according to claim 12, wherein
the rod outer surface includes a first rod inclination surface that is inclined less than 90° with respect to the virtual plane, and a second rod inclination surface that is inclined less than 90° with respect to the virtual plane.

16. The treatment instrument according to claim 12, wherein
the rod outer surface further includes a rod intermediate surface that is provided between the first apex and the second apex in the width direction.

* * * * *